(12) United States Patent
Camps et al.

(10) Patent No.: US 7,157,239 B2
(45) Date of Patent: Jan. 2, 2007

(54) METHOD AND KIT FOR IDENTIFYING AND/OR QUANTIFYING RADIOLABELED AMINOGLYCOSIDE BINDING MOLECULES

(75) Inventors: Montserrat Camps, Versoix (CH); Christian Chabert, Onex (CH); Dominique Perrin, Valleiry (FR); Thierry Martin, Collonges-sous-Salève (FR); Matthias Wymann, Bern (CH); Christian Rommel, Geneva (CH)

(73) Assignee: Applied Research Systems Ars Holding N.V., Curacao (NL)

( * ) Notice: Subject to any disclaimer, the term of this patent is extended or adjusted under 35 U.S.C. 154(b) by 77 days.

(21) Appl. No.: 10/480,310

(22) PCT Filed: Jun. 6, 2002

(86) PCT No.: PCT/EP02/06217

§ 371 (c)(1),
(2), (4) Date: Jun. 30, 2004

(87) PCT Pub. No.: WO02/101084

PCT Pub. Date: Dec. 19, 2002

(65) Prior Publication Data

US 2004/0219693 A1    Nov. 4, 2004

(30) Foreign Application Priority Data

Jun. 11, 2001  (EP) .................. 01113518

(51) Int. Cl.
*C12Q 1/48* (2006.01)
(52) U.S. Cl. ....................................... 435/15
(58) Field of Classification Search ............... 435/15, 435/194
See application file for complete search history.

(56) References Cited

U.S. PATENT DOCUMENTS 4,271,139 A    6/1981    Hart 6,017,763 A    1/2000    Stephens et al.
2004/0048310 A1*  3/2004  Plowman et al. ........... 435/7.1

FOREIGN PATENT DOCUMENTS

| EP | 0 154 734 A1 | 9/1985 |
|---|---|---|
| EP | 0 578 090 A2 | 12/1993 |
| GB | 2366370 A * | 3/2002 |
| JP | 61-76418 A | 4/1986 |
| WO | WO 90/08584 A1 | 8/1990 |
| WO | WO 96/35811 A1 | 11/1996 |
| WO | WO 99/31267 A1 * | 6/1999 |
| WO | WO 99/32640 A1 | 7/1999 |
| WO | WO 99/32655 A1 | 7/1999 |
| WO | WO 99/33499 A2 * | 7/1999 |
| WO | WO 00/00584 A2 * | 1/2000 |
| WO | WO 00/18949 A2 | 4/2000 |

OTHER PUBLICATIONS

McKnight R et al. Evaluation of a Method for Enzymic Radiochemical Assay of Tobramycin and Amikacin in Serum. Clinical Chemistry 27(7)1256-1261, 1981.*
Arbuzova, et al, "Fluorescently labeled neomycin as a probe of phosphatidylinoaitol-4,5-bisphosphate in membranes". Biochimica Et Biophysica. (2000) 1464:35-48.
Schroeder et al, "Modulation of RNA function in aminoglycoside". The EMBO Journal. (2000) 19(1):1-9.
Walter et al, "Aminoglycoside-RNA interactions". Current Opinion in Chemical Biology. (1999) 3:694-704.

* cited by examiner

*Primary Examiner*—Ralph Gitomer
(74) *Attorney, Agent, or Firm*—Browdy & Neimark, PLLC

(57) ABSTRACT

The present invention describes novel methods, assays and kits for identifying and/or quantifying Aminoglycoside Binding Molecules (ABMs), enzymes modifying such molecules, and compounds modulating the interaction between ABMs and either enzymes or aminoglycosides, by exploiting the scintillation proximity effect. The invention, which makes use of aminoglycoside-coated scintillating supports, can be adapted to high throughput screening formats.

18 Claims, 8 Drawing Sheets

Neomycin

Scintillant-impregnated bead

METHOD AND KIT FOR IDENTIFYING AND/OR QUANTIFYING RADIOLABELED AMINOGLYCOSIDE BINDING MOLECULES

FIELD OF THE INVENTION

The present invention relates to novel methods, assays and kits for identifying and/or quantifying Aminoglycoside Binding Molecules (ABMs), enzymes modifying such molecules, or compounds modulating the interaction between ABMs and either enzymes or aminoglycosides.

BACKGROUND OF THE INVENTION

Recent developments in the field of high-throughput screening technologies have broadened the range of applications, and a large choice of materials, formats, immobilization methods, and detection systems is now available for both in solution- and cell-based assays (Sundberg, 2000).

Novel analytical and screening technologies make often use of a solid support (in the form of plates, tubes, or beads) onto which a reactant is immobilized and then exposed to one or more reactions, generating a measurable signal on the support itself or in the reaction solution. The immobilization step gives the possibility to simplify the separation amongst different reactions and/or reagents, and may also allow the amplification of the signal. Such an effect can be obtained, for example, by impregnating the solid support with scintillant molecules that, excited by the radiation emitted from the immobilized molecules, multiply or alter consistently the signal generated by a labeling group alone (Meza, 2000).

Nowadays, a variety of inorganic or organic polymer core compositions enables the efficient immobilization of many ligands, as well as the scintillant impregnation, facilitating the separation and/or the sensitive detection, such as scintillation and wavelength-specific fluorescence or absorbance.

Amongst the solid phase assay based on these properties, the Scintillation Proximity Assay (SPA) has been widely applied to many biological assays involving the use of radiolabeled molecules like enzyme substrates, antibodies, proteins, or DNA. The technology relies on the observation that β rays emitted from molecules labeled with weak radioisotopes (such as $^3H$, $^{125}I$, $^{33}P$, $^{35}S$) travel only a limited distance in an aqueous environment before the energy is dissipated. These emissions can be detected with great sensitivity if the radioisotopically labeled molecules are brought into close proximity to solid support containing a scintillant compound (such as 2,5-diphenyloxazole), thereby causing a specific emission. Radiolabeled molecules remaining free into solution are undetected because they are too distant from the scintillating solid phase. Such support onto which the ligand is immobilized is usually a polymer (polystyrene, polyvinyltoluene, or yttrium-derived polymers), and can be in the form of microspheres (EP154734, U.S. Pat. No. 4,271,139) or 96-/384-wells microplates (EP576090).

SPA beads coated with many biologically relevant ligands are commercially available (Amersham). For example, SPA beads can enable the sensitive detection of radiolabeled antibodies using immobilized Protein A, of radiolabeled GST (Glutathione-S-Transferase) fusion proteins using immobilized glutathione, or of biotinylated radiophosphorylated kinases using immobilized streptavidin. Another SPA-based commercially available technology (Flash-Plate®, NEN Life Science Products) makes use of polystyrene microplates wherein wells are covered with a layer of polystyrene-based scintillant. It is however not known from prior art that the immobilization of aminoglycosides can be performed to establish SPA-based assays.

Aminoglycosides are hydrophilic multiply charged compounds, closely related to carbohydrates, whose backbone structure consists of an aminocyclitol ring saturated with amine and hydroxyl substitutions in specific positions. Aminoglycosides show high flexibility, high solublility in water, and relative insolublity in lipids, due to the basic, strongly polar groups they contain (Zembower et al., 1998).

The aminoglycosides can be divided into structural types based on the position of their glycosidic linkages, as well as on the presence and the substitutions of the 2-deoxystreptamine group. Certain compounds, often considered as aminoglycosides, actually do not contain aminosugars, thus the term aminocyclitol has been introduced to describe this entire group of molecules rather than the less precise "aminoglycoside" term, which is commonly accepted and used henceforth for simplicity.

Aminoglycosides like neomycin, dibekacin, gentamicin, tobramycin, kanamycin, amikacin, and streptomycin are well known for their antibiotic properties. These molecules are able to bind in vivo and in vitro a variety of biological ligands.

At the level of cellular membrane, aminoglycosides bind polyphosphoinositides, negatively charged phospholipids, which constitute a minor component of membrane bilayers, perturbing the permeability and other biochemical properties of the cell wall (Mingeot-Leclercq et al., 1992).

At the intracellular level, a growing number of nucleic acid structures, RNAs in particular, has been shown to be bound and modulated in their action by aminoglycosides. Examples of RNA targets recognized and altered by aminoglycosides are ribosomal RNAs, RNA aptamers, ribozymes, and other non-coding RNA sequences (Walter et al., 1999; Schroeder et al., 2000). Aminoglycosides can be modified by bacterial enzymes, providing resistance features to organisms that harbor these enzymes, due to the diminished antibacterial ability of the altered molecules (Llano-Sotelo et al., 2002).

The specificity of the aminoglycoside-phosphoinositide interaction has been studied at the structural level, demonstrating the involvement of both hydrophobic and hydrophilic interactions which determine also a toxic effect for the inner ear and kidney cells into patients (Schacht, 1986).

Neomycin, like other antibiotics of the same family, is known from late '70 to be efficiently bound by phosphoinositides. Such interaction has been exploited to extract and purify polyphosphoinositides from crude extracts by affinity chromatography on a support where neomycin was immobilized (Schacht, 1978). The immobilization of aminoglycosides has been achieved on solid phases like sepharose (WO9008584, JP61976418), polystyrene microtiter plates (Sachetelli et al., 1998), or medical devices (EP372130). Other applications based on the same principle are the selective separation and aggregation of liposomes containing polyphosphoinositides (Riaz et al., 1989; Van Bambeke et al., 1995), or the detection of polyphosphoinositides into cell membrane and intracellular vescicles (Arbuzova et al., 2000).

Moreover, fluorescently labeled aminoglycosides are known to be useful in screening RNA-binding compounds (WO9635811). Compositions facilitating the uptake of aminoglycoside antibiotic, and containing phosphoinositide polyphosphate or derivative and a labeled polyamine, like aminoglycosides, are known in the prior art (WO0018949). These compositions have been described as helping the visualization of the uptake and localization of aminoglycosides, the screening for compounds that minimize the cytotoxicity of aminoglycoside antibiotics to mammalian cells, for monitoring, calcium flux in a cell, and for screening of agonists and antagonists for proteins, in particular kinases, interacting with phosphoinositides. Either the aminoglycosides or phosphoinositides can be covalently bound to a fluorescent compound.

The binding properties of aminoglycosides allow the clearance of bacteria by inhibiting protein synthesis, decreasing the fidelity of messenger RNA translation, and disrupting the integrity of the bacterial cell membrane. The interaction of aminoglycosides with biological ligands, thus, has considerable physiological effects, and methods for identifying and/or quantifying Aminoglycoside Binding Molecules (ABMs), enzymes modifying such molecules, and compounds modulating the interaction between ABMs and either enzymes or aminoglycosides have many important applications, in particular if compatible with high throughput formats.

An example of physiological mechanism which can be studied by exploiting the interaction between aminoglycosides and biological ligands is constituted by the phosphorylation of cell membrane phosphoinositides.

Phosphoinositides have a basic structure, termed phosphatidylinositol, consisting of diacyl-glycerol linked by phosphodiester bond to the 1' position of an inositol head group. The acyl chains of diacylglycerol (typically stearyl-arachidodyl) are inserted into the inner leaflet of the membrane bilayer. The inositol head group, which is cytosolic, may be further phosphorylated on the 3', 4', 5', or any combination of these, by enzymes called phosphoinositide kinases (PIKs) which are specific for a single position on the inositol ring. Such different phosphorylation states characterize molecules having highly specific properties. In particular, the phosphoinositide 3-kinases (PI3Ks) form a family of ubiquitously expressed enzymes that, through phosphorylating membrane inositol lipids in the 3' position of the inositol ringl and the consequent generation of phospholipid second messengers, play a key role in the regulation of many cellular processes (such as motility, proliferation, differentiation, apoptosis, membrane transport, and carbohydrate metabolism), representing one of the major pathways of intracellular signal transduction (U.S. Pat. No. 6,017,763; Leevers et al., 1999; Stein and Waterfield, 2000; Hinchliffe, 2001; Comer and Parent, 2002; Simonsen et al., 2001).

To date, eight mammalian PI3Ks have been identified, divided into three main classes (I, II, and III) on the basis of sequence homology, structure, binding partners, mode of activation, and substrate preference in vitro. All PI3Ks share a kinase domain located towards the C-terminus of the enzyme, a scaffold-like helical region, and a C2 domain known to bind phospholipids. The N-terminus of the enzyme, where interactions with adapter subunits and other proteins are believed to occur, is highly variable. Many other enzymes have been identified whose catalytic domains closely resemble those of PI3Ks, like the phosphoinositide 4-kinases (PI4Ks), DNA-dependent protein kinases, and the mTOR kinase.

Even though other phosphatidylinositols having a 3' group available for the phosphorylation can be modified by PI3Ks, the major cellular substrate is phosphatidylinositol (4,5)-bisphosphate (also indicated as PtdIns(4,5)P2, PIP2 or $PI_{(4,5)}P2$). Upon activation of PI3K by several G Protein Coupled Receptors (GPCR) agonists, growth factors or inflammatory cytokines, $PI_{(4,5)}P2$ is converted into phosphatidylinositol (3,4,5)-trisphosphate (also indicated as $PI_{(3,4,5)}P3$, PtdIns(3,4,5)P3, or PIP3). This latter molecule has been characterized in vivo as a second messenger responsible for a wide variety of signaling events including phosphorylation and activation of several downstream effectors of PI3K. Moreover, several proteins, containing the Pleckstrin homology (PH) or the Phox homology (PX) domains and requiring membrane association for their function, interact directly with the cell membrane by binding to phosphoinositides with a broad range of specificity and affinity for different phosphorylation state (Xu et al., 2001).

Four class I PI3Ks ($\alpha,\beta,\gamma$, and $\delta$ isoforms) have been described in humans and other mammals in connection with distinct or overlapping cellular functions, and are the PI3Ks better characterized at both structural and functional level. PI3K$\alpha$, PI3K$\beta$ and PI3K$\delta$ are widely expressed and activated by interacting, through SH2 domain-containing adapter molecules, with growth factor receptor tyrosine kinases and other intracellular phosphotyrosine-containing proteins. In contrast, PI3K$\gamma$ is only expressed in hematopoietic cells (especially in leukocytes), and it is the only isoform that has been shown to respond, through an adapter molecule not containing the SH2 domain, to G-protein coupled receptors through the interaction and activation with G-protein $\beta\gamma$-subunits. Interestingly, mice lacking PI3K$\gamma$ show, amongst other phenotypes, a clear defect in leukocyte migration and are less susceptible of septic shock, suggesting a role of PI3K$\gamma$ on cell migration (Hirsch et al., 2000). The functional specialization of PI3K isoforms suggests that isoform-selective inhibition with acceptable side effects might be possible and therapeutically useful in many conditions. PI3K$\gamma$ appears as an attractive drug target candidate for the treatment of inflammatory processes involving leukocyte migration, as malignant diseases and other diseases with an inflammatory or immune component.

Two molecules have been mostly studied as PI3Ks inhibitors: Wortmannin, previously known as an inhibitor of respiratory-burst activity (Arcaro and Wymann, 1993) and LY294002 (Powis et al., 1994). Although Wortmannin and LY294002 have been widely used to elucidate the biological functions of PI3Ks activation at a cellular level in short term assays, these compounds have specific properties limiting their pharmaceutical potential. Both Wortmannin and LY294002 show a poor selectivity, since different class I kinases are inhibited at comparable concentrations (Stein and Waterfield, 2000). Moreover, Wortmannin, binds PI3K$\gamma$ ATP-binding site irreversibly at nanoMolar concentrations but it is a molecule quite unstable, while LY294002 binds PI3K$\gamma$ ATP-binding site competitively at microMolar concentrations but it is a molecule with solubility problems. A number of chemical modifications of Wortmannin and LY294002 have been made, only a few of them providing molecules significantly more potent than the parent compound (Creemer et al., 1996).

Various technologies have been tested for improving the throughput of screening for PI3K$\gamma$, or other PI3K related kinases, and identify more potent and specific inhibitors. All these methods have in common the incubation of the kinase with a substrate (usually phosphoinositide), a radiolabeled precursor ([$\gamma$-$^{32}$P] ATP or [$\gamma$-$^{33}$P] ATP) and the potential inhibitor, but the way these basic components are arranged or modified to establish the assay can have a profound effect on the throughput and the sensibility of the assay.

The prior art discloses different systems for identifying compound interfering with the phosphorylation activity of PI3K-related kinases, by means of antibodies specific for a moiety conjugated to the potential inhibitor (WO9855602), the analysis of alterations in motility of cells exposed to the potential inhibitor (WO9935283), lipid extraction combined to chromatographic separation (Ward, 2000), directly labeled aminoglycosides (WO0018949), or thin layer chromatography (Frew et al., 1994). Such assays are laborious to carry out, difficult to automate and generate problems and expenses due to the radioactive waste.

Some high throughtput screening technologies have been developed for studying enzymes modifying phosphoinositides. FlashPlate® microplates covered with [$^3$H] PI$_{(4,5)}$P2 have been generated by incorporating this molecule through covalent attachment and/or by hydrophobic interaction and used to test Phospholipase C, an enzyme that catalyzes the hydrolysis of phosphoglycerides into diacylglycerols and phosphorylated alcohols. The assay, however, measures the reduction of radioactivity in the microplate due to the generation of [$^3$H]-inositol which migrates in the acqueous phase and then is removed (WO9932655). Alternatively, phosphoinositide have been bound covalently on the scintillant substrate using a linker moiety, like polyethylene glycol or succinimide, providing composition useful for assaying phosphatidylinositol kinases and for screening compounds inhibiting these enzymes. (WO0000584).

However there is no indication that aminoglycoside covered scintillating supports can be used as a general tool for identifying and/or quantifying Aminoglycoside Binding Molecules (ABMs), enzymes modifying such molecules, compounds modulating the interaction between ABMs and either enzymes or aminoglycosides.

SUMMARY OF THE INVENTION

It has now been demonstrated that aminoglycosides immobilized on a scintillating solid support allow the effective immobilization and detection of appropriately radiolabeled groups added or cleaved to an Aminoglycoside Binding Molecule (ABM), by measuring the scintillation proximity signal consequently generated.

Thus, it is an object of the present invention a method for identifying and/or quantifying radiolabeled Aminoglycoside Binding Molecules (ABMs) into a sample, said method comprising the following steps:
a) preparing a sample comprising at least an ABM and an enzyme;
b) allowing said enzyme either to add a radiolabeled group present in the sample to the ABM, or to cleave a radiolabeled group already present in the ABM;
c) incubating the sample with one or more solid supports impregnated with a scintillating compound and covered with an aminoglycoside; and
d) measuring the scintillation proximity signal generated by said support(s).

Depending on the criteria and/or the reactants used in the preparation of the sample, the method can be applied to various embodiments, wherein samples prepared with the same criteria are compared by measuring the emission generated in each sample due to the proximity between the scintillating support and the radiolabeled ABM.

In a preferred embodiment, the present invention provides an assay for identifying and/or quantifying compounds modulating the interaction between an ABM and an enzyme capable either of adding a radiolabeled group present in the sample to the ABM, or of cleaving a radiolabeled group already present in the ABM, by comparing the scintillation proximity signal generated by aminoglycoside-coated scintillating support(s) incubated with different samples prepared according to step (a) and comprising equal amount of the ABM, equal amount of the enzyme, with or without one or more additional compounds.

In another preferred embodiment, the present invention provides an assay for identifying and/or quantifying compounds modulating the interaction between an ABM and an aminoglycoside by comparing the scintillation proximity signal generated by aminoglycoside coated scintillating support(s) incubated with different samples prepared according to step (a) and comprising equal amount of the ABM, equal amount of the enzyme, with or without one or more additional compounds added before or during step (c).

In a still preferred embodiment, the present invention provides an assay for identifying and/or quantifying an enzyme capable either to add a radiolabeled group present in the sample to the ABM, or to cleave a radiolabeled group already present in the ABM, by comparing the scintillation proximity signal generated by aminoglycoside coated scintillating support(s) incubated with different samples prepared according to step (a) and comprising equal amount of the same ABM and different mixture of molecules potentially containing such enzyme.

In a further embodiment, the present invention provides an assay for identifying and/or quantifying an ABM, by comparing the scintillation proximity signal generated by aminoglycoside coated scintillating support(s) incubated with different samples prepared according to step (a) and comprising equal amount of the same enzyme and different mixture of molecules potentially containing an ABM.

The previously described assays can be applied in a direct or competitive manner, by adding compounds that compete with, or alter, one of the components included in the assay, such as an ABM other than the one used in step (a) and (b) or an aminoglycoside-modifying enzyme. Moreover, these methods makes possible screening of samples in an high throughput format for assaying, for example, potential inhibitors of phosphoinositide 3-kinase making use of scintillating beads coated with neomycin.

In a further embodiment, the present invention provides scintillating solid supports coated with an aminoglycoside and their use for identifying and/or quantifying radiolabeled Aminoglycoside Binding Molecules into a sample.

Finally, the present invention provides a kit for identifying and/or quantifying Aminoglycoside Binding Molecules (ABMs), enzymes modifying such molecules, or compounds modulating the interaction between ABMs and either enzymes or aminoglycosides, comprising a scintillating solid support covered with an aminoglycoside.

DETAILED DESCRIPTION OF THE INVENTION

Figure 1:
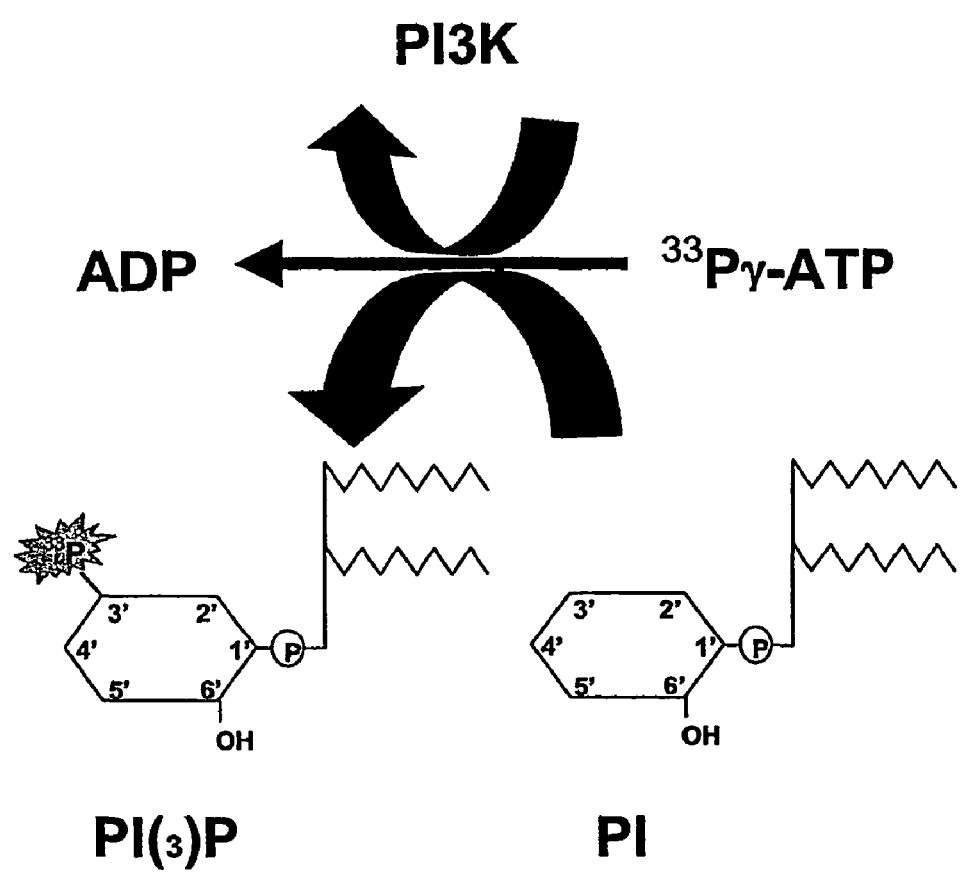
FIG. 1 shows the reaction driven by PI3Ks performed in the examples. These enzymes bind and hydrolyse the substrate ATP, originating ADP and a free phosphate group which is transferred to the 3' position of the inositol ring of phosphatidyl inositol (PI), generating PI$_{(3)}$P. If the ATP is actually provided in the form of [$^{33}$P]γ-ATP, the radiolabeled terminal phosphate group is transferred on the phospholipid. The reaction is performed in vivo on PI$_{(4,5)}$P2, giving rise to the signaling molecule PI$_{(3,4,5)}$P3.

The present invention combines the knowledge about the affinity of aminoglycosides for specific classes of molecules with the technologies based on the signal amplification due to the proximity between β rays emitting isotopes and scintillant supports. The specificity and the strength of the aminoglycoside mediated interactions allow the highly reliable identification of the scintillation proximity signal generated between an appropriately labeled ABM and the support once that the sample to be analyzed is put in contact with a scintillating solid support covered with the aminoglycoside. Once understood the basic principles, the invention can be applied in various analytical methods and uses involving ABMs and enzymes capable either to add a radiolabeled group present in the sample to the ABM, or to cleave a radiolabeled group already present in the ABMs.

The methods of the present invention allows the identification and/or the quantification of radiolabeled Aminoglycoside Binding Molecules (ABMs) into a sample, comprise the following steps:
a) preparing a sample comprising at least an ABM and an enzyme;
b) allowing said enzyme either to add a radiolabeled group present in the sample to the ABM, or to cleave a radiolabeled group already present in the ABM;
c) incubating the sample with one or more solid supports impregnated with a scintillant compound and covered with an aminoglycoside;
d) measuring the emission generated by the scintillating support(s).

By changing the criteria and/or the reactants used in the preparation of the sample in step (a) and comparing different samples, the present invention can be applied to assay the presence and the activity of various molecules, as it will be evident during the description.

Aminoglycoside Binding Molecules (ABMs) are intended all the compounds that, when appropriately radiolabeled, interact with any aminoglycoside coated scintillating support with an affinity sufficient to allow the generation of a specific scintillation proximity signal. The specificity of this signal can be determined by comparing the signal obtained by using scintillating support with other kinds of moieties, but there are two main classes of biological compounds that showed a strong affinity for immobilized aminoglycosides, and that can be in vivo and in vitro modified with a radiolabeled group compatible with a scintillation proximity assay: nucleic acids (RNAs in particular) and phospholipids.

RNA molecules having various origins and structure (including ribozymes, ribosomal RNAs, RNA aptamers, and other non-coding RNAs) have shown a strong affinity for one or more aminoglycosides (Walter et al., 1999; Schroeder et al., 2000). Each RNA species is not bound by all aminoglycosides with the same affinity and in the same manner. Therefore, depending on the RNA and/or the RNA modifying enzyme (being a protein or another RNA) is intended to be studied, an appropriate RNA is included in the sample and an appropriate aminoglycoside is immobilized on the scintillating support. Prior art shows several examples of specific RNA-aminoglycoside complexes (Wang et al. 1996; Hamasaki et al. 1998; Cho and Rando, 1999).

The phospholipid-aminoglycoside interactions and the effect of aminoglycosides on phospholipid modifying enzymes have been studied and exploited since many years (Schacht, 1986; Mingeot-Leclercq et al., 1992). Several enzymes, capable of modifying phospholipids by adding or cleaving chemical groups (such as phospholipid kinases, phosphatases, and lipases) have been identified and associated to important biological functions (Leevers et al., 1999; Stein and Waterfield, 2000). As said for RNAs, depending on the phospholipid and/or the phospholipid-modifying enzyme is intended to be studied, the composition of the sample and the immobilized aminoglycoside can vary accordingly.

The radiolabeled group can be added to the ABM either using chemical synthesis or an enzyme, which can transfer it from an appropriate precursor. The chemical addition of the radiolabeled group can be preliminary to preparation of the sample comprising an enzyme cleaving the ABM in a way that the scintillation proximity effect is abolished. The enzymatic addition of the radiolabeled group can be either preliminary to the reaction described for the chemical addition or actually performed before exposing the sample to the aminoglycoside-coated scintillating support.

It is suitable for the present invention any isotope that can be included in a chemical group to generate a radiolabeled group, being said group compatible with the ABM, the enzyme, and the ABM-aminoglycoside interaction. Once incorporated in the ABM, the radiolabeled group should emit the radiation energy activating the scintillating support when the ABM is bound to the immobilized aminoglycoside. If the radiolabeled group is not incorporated in the ABM, it will be generally too far removed from the scintillating support to enable the radioactive energy to activate the scintillant. Therefore, the measurement of a specific scintillation proximity signal can be performed even without separating the support from the sample from. It is possible, however, to separate the support from the sample using any suitable mean before measuring the scintillating proximity signal, for example by centrifuging the supports and removing the liquid phase.

Using RNA and phospholipids as examples of ABMs, a suitable isotope is $^{33}$P, which can be easily incorporated as radiolabeled phosphate group, starting from [γ-$^{33}$P] ATP, either in the nucleic acid backbone or in the inositol ring. However, other isotopes known to provide a scintillation proximity effect (such as $^3$H, $^{125}$I, or $^{35}$S) can be also used for generating the radiolabeled group.

The present invention can be applied using any kind of scintillant solid support allowing the effective immobilization of aminoglycosides. The prior art (EP154734, EP576090, U.S. Pat. No. 4,271,139, U.S. Pat. No. 3,018,178, EP556005) and manufacturers (Amersham, NEN) offer many examples of solid phases impregnated with various scintillant compounds, usually polymeric compounds (polyvinyltoluene, polystyrene) shaped in the form of beads or microplates, but any other suitable form can be applied. As said beforehand, the use of beads or microplates considerably improves the throughput of the methods of the invention, which are particularly useful to perform the parallel analysis of many samples (up to several thousands), an approach not feasible for a number of enzymes involving ABMs.

Methods and reagents allowing the effective and stable immobilization of aminoglycosides (and, in general, of aminated biological ligands) on a solid phase have been disclosed in the prior art for a variety of supports and polymers (Sachetelli et al., 1998; WO9008584; EP372130, EP350407). Generally, these methods comprise the incubation of the aminated ligand with the solid phases simultaneously or after a compound or a buffer activates the solid phases or the aminated ligand. This coupling reaction can then be followed by another reaction in which the unreacted groups are blocked and/or the fixation of the ligand is stabilized.

As explained in the prior art (WO9933499), when an aldehyde moiety (RCHO, located on the support) reacts with a primary amine moiety (R'NH$_2$, located on the aminoglycoside), an equilibrium is set up with the reaction product, which is a relatively unstable imine moiety (R'N=CHR). This linkage can be stabilized by a reductive alkylation of the imine moiety using reducing agents (i.e., stabilizing agents) such as sodium borohydride or sodium cyanoborohydride, thus forming form a secondary amine (R'NH—CH2R). The coupling and stabilizing reactions are usually performed at a pH comprised between 6 and 10, and a temperature comprised between 4° C. and 37° C., and they are completed within 24 hours. Any other method and protocol allowing the effective covalent (or non-covalent) immobilization of aminoglycosides on a scintillating support during all the manipulations or reactions is suitable for the methods and the uses of the present invention.

Once that the samples comprising radiolabeled ABMs have been prepared using whatever method, they can be exposed to the aminoglycoside-coated supports for a time sufficient for achieving the binding to the support, and then the scintillation proximity signal is measured for each sample, according to the methods disclosed in the prior art and to commercially available counters (Wallac). Optionally, compounds blocking the enzymatic reaction can be added to the samples before incubating them with the scintillating supports, but the presence of aminoglycoside already inhibits many of these reactions. The comparison amongst the values obtained for the different samples should provide an information on the efficiency of the enzyme in each sample.

However, different experimental designs can be elaborated taking advantage of the methods of the invention for characterizing various kinds of molecules and of information.

The methods of the invention can be applied in assays for identifying and/or quantifying compounds modulating the interaction between a substantially pure ABM and either a substantially pure enzyme or the aminoglycoside. By comparing the scintillation proximity signal associated to the aminoglycoside-coated scintillating supports, different compounds, or mixtures of compounds (such as a library or chromatographic fraction), can be characterized and/or purified as having, for example, a specific inhibiting activity.

In a first group of experimental designs, each sample should contain equal amount of the ABM, an enzyme capable of transferring a radiolabeled group on the ABM, a precursor containing this radiolabeled group, and one or more additional compounds, for example potential inhibitors of the enzyme. Alternatively, equal amounts of an ABM already chemically or enzymatically radiolabeled are mixed in the each sample with equal amounts of an enzyme capable of cleaving the radiolabeled ABM in a way that radiolabeled group is separated from the moiety responsible of interaction with aminoglycosides, and with one or more additional compound which are potential inhibitors of the enzyme. Also in this case, the comparison with a control sample allow to identify and/or quantify the inhibition of the enzyme due to these additional compounds using the methods of the invention.

By comparing a control sample with the other samples, the inhibition of the enzyme due to these additional compounds can be identified and/or quantified by the methods of the invention as reduction of the scintillation proximity signal, as the examples show in the case of compounds inhibiting a kinase phosphorylating a specific position into a phospholipid. Alternatively, such compounds can be phosphoinositides-binding proteins (Xu et al., 2001).

In a second group of experimental designs, the additional compounds are supposed to inhibit the interaction between the ABM and the aminoglycoside. By comparing a control sample with samples in which additional compounds are added once that the radiolabeling reaction is completed (before or during step (c)), a decrease in the measured scintillation proximity signal suggests that the compounds affect the interaction between the ABM and the aminoglycoside immobilized on the scintillating support. This is the case if an ABM other than the one used in step (a) and (b) or an aminoglycoside-modifying enzyme is added, or if an aminoglycoside-modifying bacterial enzyme is added (Llano-Sotelo et al., 2002).

In another situation, either the ABM or the enzyme can be actually in an insufficiently purified form since they derive from library or chromatographic fractions. In this case, the increase or the decrease of the measured scintillation proximity signal suggests that a particular fraction may be enriched in a specific enzyme (using a standardized radiolabeled ABM in all samples) or in a specific ABM (using a standardized enzyme and radiolabeling reaction).

All the previously described methods can be applied in a direct or competitive manner, by adding compounds that compete with, or alter, one of the components present into the sample. Such molecules can be included in the assay to verify their effect on the kinase activity and/or the interaction with aminoglycosides, or with the scope to charatcterize and/or quantify these molecules and their properties.

The previous methods can be comprised in screening assays and kits for analyzing samples in a high throughput format. The scintillating solid supports coated with an aminoglycoside disclosed in the present invention can be used for identifying and/or quantifying a radiolabeled aminoglycoside binding molecule into a sample and in kits for identifying and/or quantifying aminoglycoside binding molecules, enzymes modifying said molecules, or compounds modulating the interaction between ABMs and either enzymes or aminoglycosides a radiolabeled aminoglycoside binding molecule into a sample.

The following examples are intended to illustrate the invention using neomycin coated SPA beads (as scintillating supports), human recombinant PI3Kγ fused to glutatione-S-transferase (as enzyme), phoshophoinoside (as aminoglycoside binding molecule), and [$^{33}$P]γATP (as precursor providing the radiolabeled group), with or without compounds inhibiting the enzyme. The invention shows to provide means to perform an in vitro assay for PI3Ks inhibitors based on SPA beads, which is particularly robust and reproducible in a typical format for high throughput assays (96 or 384 wells microtiter plates).

The present invention has been described with reference to the specific embodiments, but the content of the description comprises all modifications and substitutions which can be brought by a person skilled in the art, without extending beyond the meaning and purpose of the claims. The examples should not be construed as in any way limiting the applicability and the usefulness of the invention as disclosed.

EXAMPLES

1. Materials & Methods

Preparation of Neomycin-Coated SPA Beads

Polyvinyltoluene SPA beads (100 milliliters of a 100 milligrams/milliliter suspension; Amersham) are centrifuged at 4400×g for 10 minutes. The supernatant is removed and pelletted beads are resuspended in 100 milliliters of borate buffer (pH 8.5). After being mixed with a roller mixer for 15 minutes, the suspension is centrifuged 4400×g for 10 minutes and resuspended in 100 milliliters borate buffer having the same pH twice. Beads are then resuspended in 100 milliliters of 50 milliMolar neomycin sulfate (pH 8.5). The pot containing the suspension is covered with foil and incubated overnight in a roller mixer at room temperature. The suspension is then transferred in glass beakers, where 150 milligrams of sodium borohydrade are added, mixed for a further 3 hours at room temperature, and finally centrifuged at 17600×g for 15 minutes. After being resuspended with 100 milliliters of bidistilled water and centrifuged at 17600×g for 15 minutes three times and with 100 milliliters of 1% sucrose further three times, the beads are finally resuspended in 50 milliliters of 1% sucrose. The beads concentration in the suspension is determined using a gravimetric assay and the concentration was then adjusted to 100 milligrams/milliliter before being dispensed in 500 milligrams aliquots and freeze-dried.

Samples of the supernatant are taken during the manufacturing steps after the overnight incubation with neomycin sulfate, filtered, and the amount of neomycin present is estimated fluorometrically using the fluorescamine assay (Lorenzen and Kennedy, 1993). Fluorescamine is a molecule that, in presence of amine groups, reacts rapidly and generate fluorescent groups. A standard curve is plotted by reacting known amount of neomycin (up to 1.5 milligrams/milliliter) with fluorescamine, and using this curve the amount of neomycin actually immobilized on the beads is estimated to 36 micrograms per milligram of beads.

Immobilization procedures using higher amount of neomycin sulfate (150 milliMolar) and/or borate buffer at higher pH (pH 10.0) lead to the immobilization of neomycin in comparable amount (19–127 micrograms per milligram of beads).

Preparation of Human Recombinant PI3Kγ

The enzyme used in the examples is expressed as a recombinant fusion protein with glutathione-S-transferase (GST; a moiety that allows a quick and efficient purification by affinity chromatography) using a Baculovirus/Sf9 insect cells system as previously described (WO9612024), with the only difference that the cDNA fragment cloned into the vector pAcG2T misses the segment coding for the first 36 amino acids of human PI3Kγ (SWISSPROT Acc. No. P48736), which is expressed starting from the Isoleucine in position 37. Expression and purification of the recombinant protein are carried out using standard protocols for GST fusion proteins. Alternative forms of this enzyme are known and can be used as well (WO9740173, WO9625488).

Preparation of Phospholipids

Even though PI is not PI$_{(4,5)}$P, the molecule converted in vivo by PI3Kγ in the signaling molecule PI$_{(3,4,5)}$P, the conversion rate of PI into PI$_{(3)}$P is commonly considered as well indicative of the in vitro activity of the enzyme (FIG. 1).

The phospholipidic substrate is prepared as micelles containing a mixture of 100 microMolar phosphatidyl inositol (PI; Fluka) and 250 microMolar phosphatidyl serine (PS; Fluka). The phospholipids are evaporated to dryness under a nitrogen stream in a borosilicate glass tube. The lipids are then resuspended in Hepes 40 milliMolar (pH 7.4) by vortex-mixing for 20 minutes and then sonicated into a water bath (Branson 2500) for 15 minutes.

Kinase Inhibitors

The non-specific and specific kinase inhibitors tested for verifying the reliability of the methods based on neomycin-coated SPA (Wortmannin, LY2924002, Rapamycin) are commercially available (Upstate Biotechnology).

2. PI3Kγ Assay Using Neomycin-Coated SPA Beads

Figure 2:
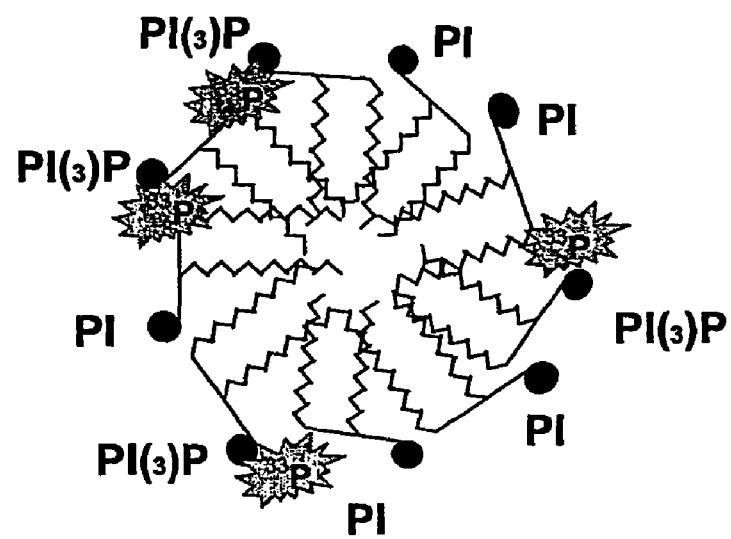
FIG. 2 shows the lipid micelles formed by the aggregation of labeled and unlabeled phosphoinositols.
Figure 3:
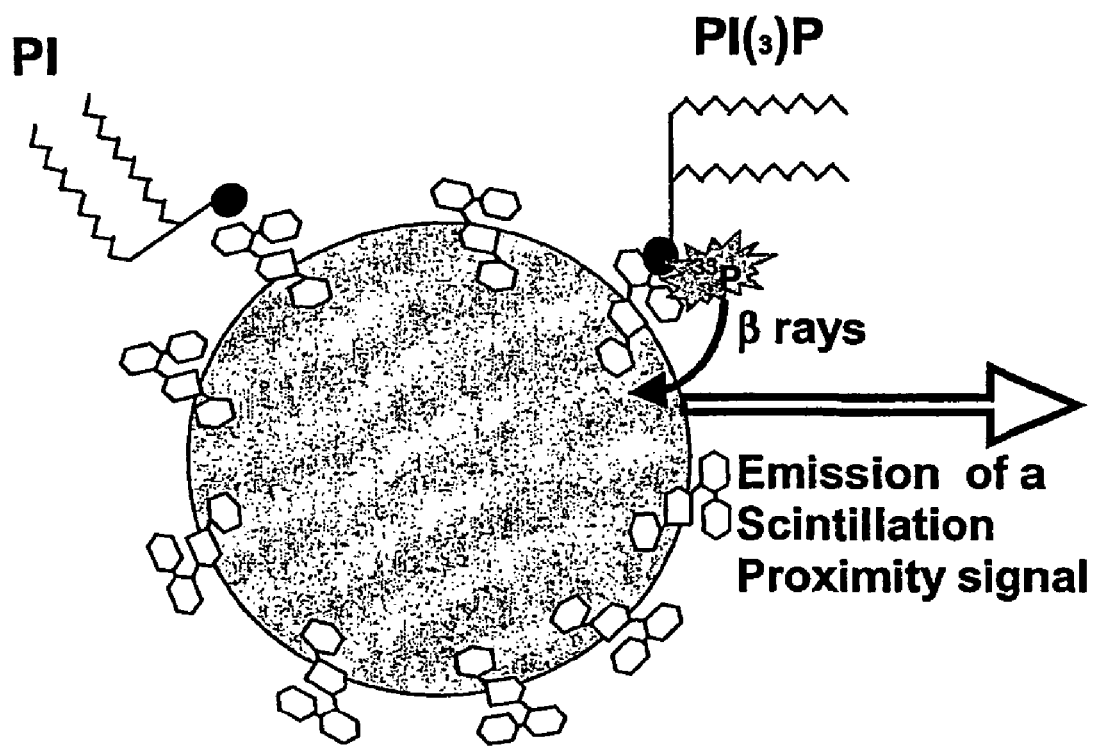
FIG. 3 shows the interaction between a SPA bead and labeled or unlabeled phosphoinositols, wherein only the latter one produces a detectable emission. Even if a single molecule of non-/radiolabeled PI$_{(3)}$P is represented, the interaction can be determined also by the interaction of beads with micelles as shown in FIG. 2.
Figure 3:
Figure 3:
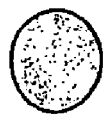

Since this kind of assays is mainly exploited in high throughput screenings, the protocol has been developed to allow the assay to be performed into standard 384-/96-wells microtiter plates. In the specific case of high throughput screening for compounds inhibiting PI3Kγ, the samples contain human recombinant GST-PI3Kγ, the phospholipid micelles, radiolabeled ATP and, optionally, the compounds to be tested as inhibitors of the enzyme, all these components mixed into an appropriate buffer. The reaction leads to a more or less important radiolabeled fraction of the phospholipids aggregated into micelles (FIG. 2). The neomycin-coated SPA beads are then added, blocking the reaction and interacting with all phospholipids strongly enough to immobilize them on their surface (FIG. 3). The quantification of the scintillation proximity signal obtained from the labeled PI$_{(3)}$P immobilized on the beads allows an evaluation of the kinase activity in different samples.

Depending on the dimension of the microplate well, the total volume of the reaction can be adapted. While a 96-well microplate format allows the manipulation of volumes down to 50 microliters, the 384-well microplate format allows a reduction of the sample volume down to 30 microliters. Table I shows the volume of each reaction component to be mixed for obtaining three different final volume (all the volumes are expressed in microliters).

TABLE I

| | | | |
|---|---|---|---|
| Human recombinant GST-PI3Kγ | 5 | 10 | 10 |
| Phospholipid micelles | 10 | 10 | 50 |
| Kinase buffer | 10 | 20 | 30 |
| Inhibiting compound (or water, in control reactions) | 5 | 10 | 10 |
| Final volume | 30 | 50 | 100 |

The enzyme is dissolved in 40 milliMolar Hepes (pH 7.4), 1 milliMolar DTT (dithiothreitol) and 5% ethylene glycol. The amount of the enzyme added in each sample obviously affects the quantity of radiolabeled substrate, but it is usually comprised between 7.5 and 100 nanograms per sample.

The final concentration of the kinase buffer component is from 10 to 40 microMolar/200 nanoCurie [$^{33}$P]γ-ATP, 10 milliMolar MgCl$_2$, 1 milliMolar DTT, 1 milliMolar β-glycerophosphate, 100 microMolar NaVO$_4$, 0.1% sodium cholate, 40 milliMolar Hepes (pH 7.4). DMSO (dimethyl sulfoxide) can be also present for improving the solubility of the inhibiting compound but it should not exceed a final concentration of 1% to avoid a spurious inhibitory effect on the kinase.

After an incubation at room temperature for a period ranging from 45 to 180 minutes, with gentle agitation, the reaction is stopped by addition of 60 microliters (sample volume of 30 microliters) or 180 microliters (sample volume of 50 or 100 microliters) of phosphate-buffered saline (PBS) buffer containing unlabeled 10 milliMolar ATP (competing for non-specific binding with the labeled one still present), 5 milliMolar ethylene-diamine-tetraacetic acid (EDTA, a compound inhibiting the kinase) and 100 micrograms (250 micrograms for the reaction volume of 50 or 100 microliters) of the neomycin-coated polyvinyltoluene SPA beads.

After an incubation of 60 minutes, at room temperature and with gentle agitation, the neomycin-SPA beads are then recovered by centrifuging the plates for 5 minutes at 1500× g, and removing the supernatant. The amount of radioactive PI($_3$)P formed in each well is quantified by scintillation counting in a MicroBeta™ plate counter (Wallac). The quantification has been done in dpm (desintegration per minute) instead of cpm (counts per minute) to take into account the fact that the cpm corresponds exactly to dpm only if the beta counter has a 100% efficiency in measuring the desintegration events. When this cannot be guaranteed, a correction factor is included in the calculations, wherein 1 Curie corresponds to 2.22×10$^{12}$ dpm.

In order to demonstrate the efficacy of the detection method, improve the throughput of the assay, and increase the signal/background ratio in the microplate-based format, various conditions have been tested by titrating different assay components.

Figure 4:
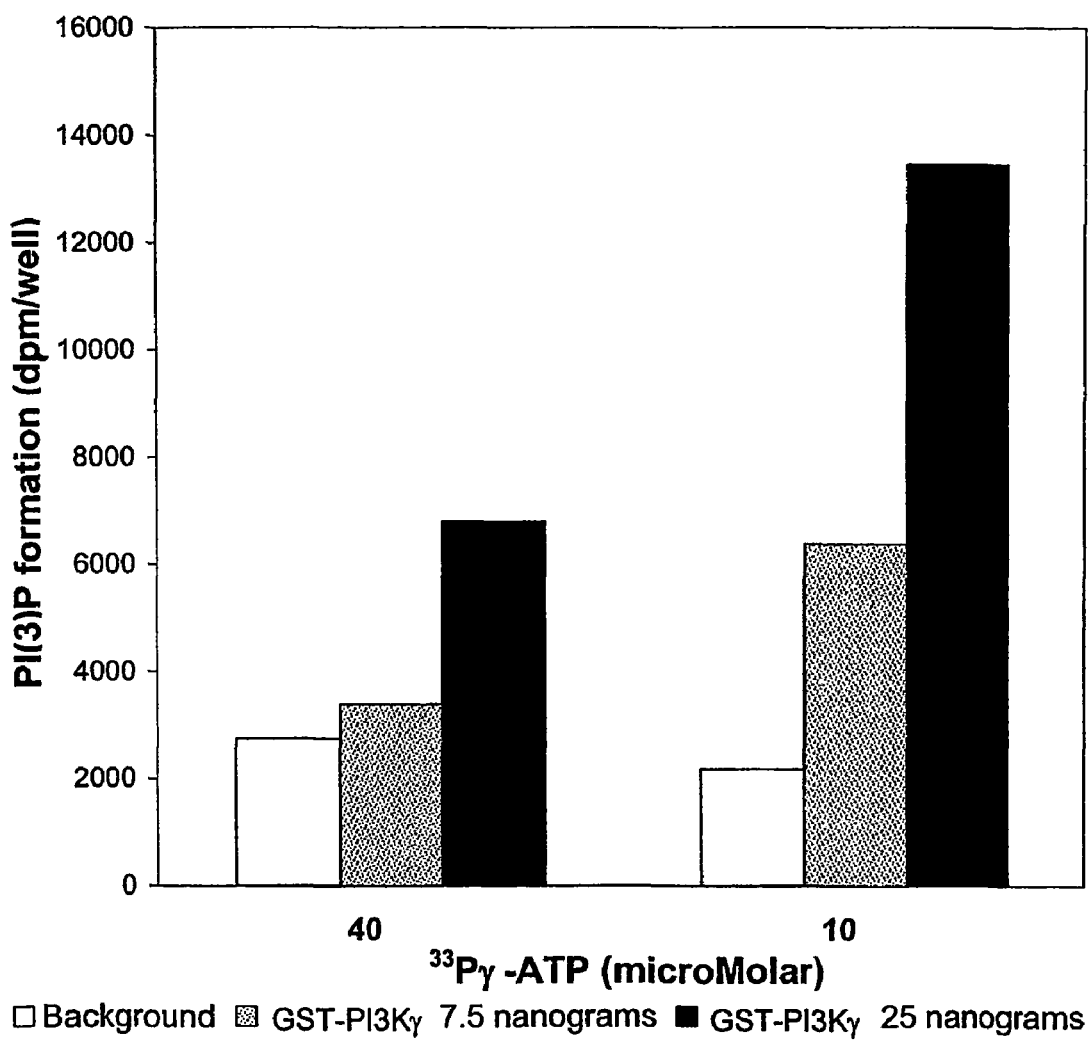
FIG. 4 shows that the radiolabeled PI$_{(3)}$P measured using the neomycin-SPA beads and obtained using different concentrations of [$^{33}$P]γ-ATP and of human recombinant GST-PI3Kγ. The final volume of the sample is 100 microliters. Neomycin-coated SPA beads are incubated 60 minutes after that the reaction proceeded for 45 minutes.
Figure 5:
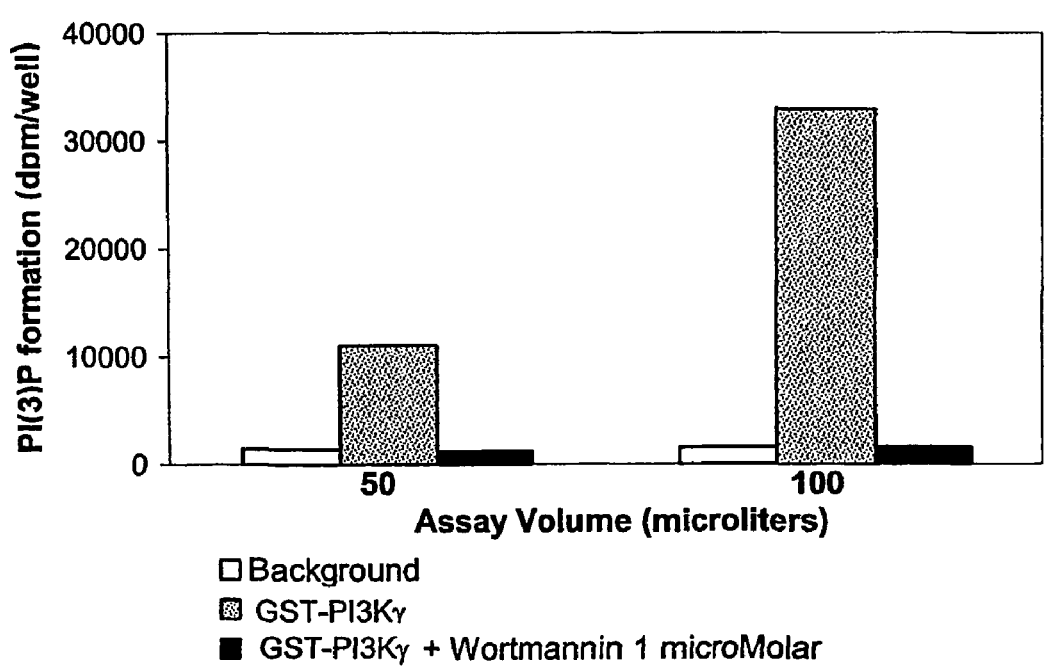
FIG. 5 shows the effect of assay volume on the PI$_{(3)}$P background/signal ratio formation, in absence or presence of 1 micromolar Wortmannin. The amount of recombinant GST-PI3Kγ is 25 nanograms.

It has been found that the reduction of [$^{33}$P]γ-ATP concentration from 40 to 10 microMolar/200 nanoCurie results in a two-fold increase in the signal/background ratio, especially in presence of smaller amount of kinase (FIG. 4). As shown by comparing the counts obtained using two different amounts of the kinase, the specific signal is proportional to the enzyme concentration. The reduction of the volumes from 100 microliters to 50 microliters further improves such ratio (FIG. 5).

Figure 6:
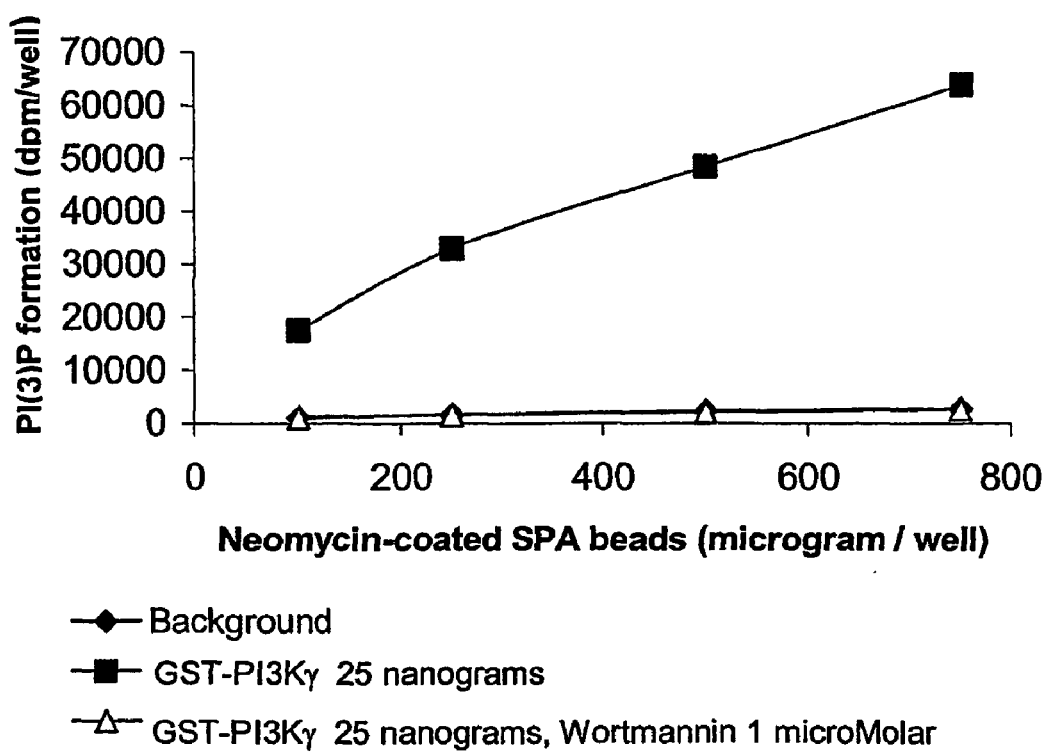
FIG. 6 shows the titration of neomycin-coated SPA beads using [$^{33}$P]γ-ATP and GST-PI3Kγ, and in absence or presence of an inhibitor, Wortmannin. The sample contains 25 nanograms of GST-PI3Kγ, in a final volume of 50 microliters. After incubation at room temperature for 45 minutes, increasing amounts of neomycin-coated SPA beads are added to each well.
Figure 7:
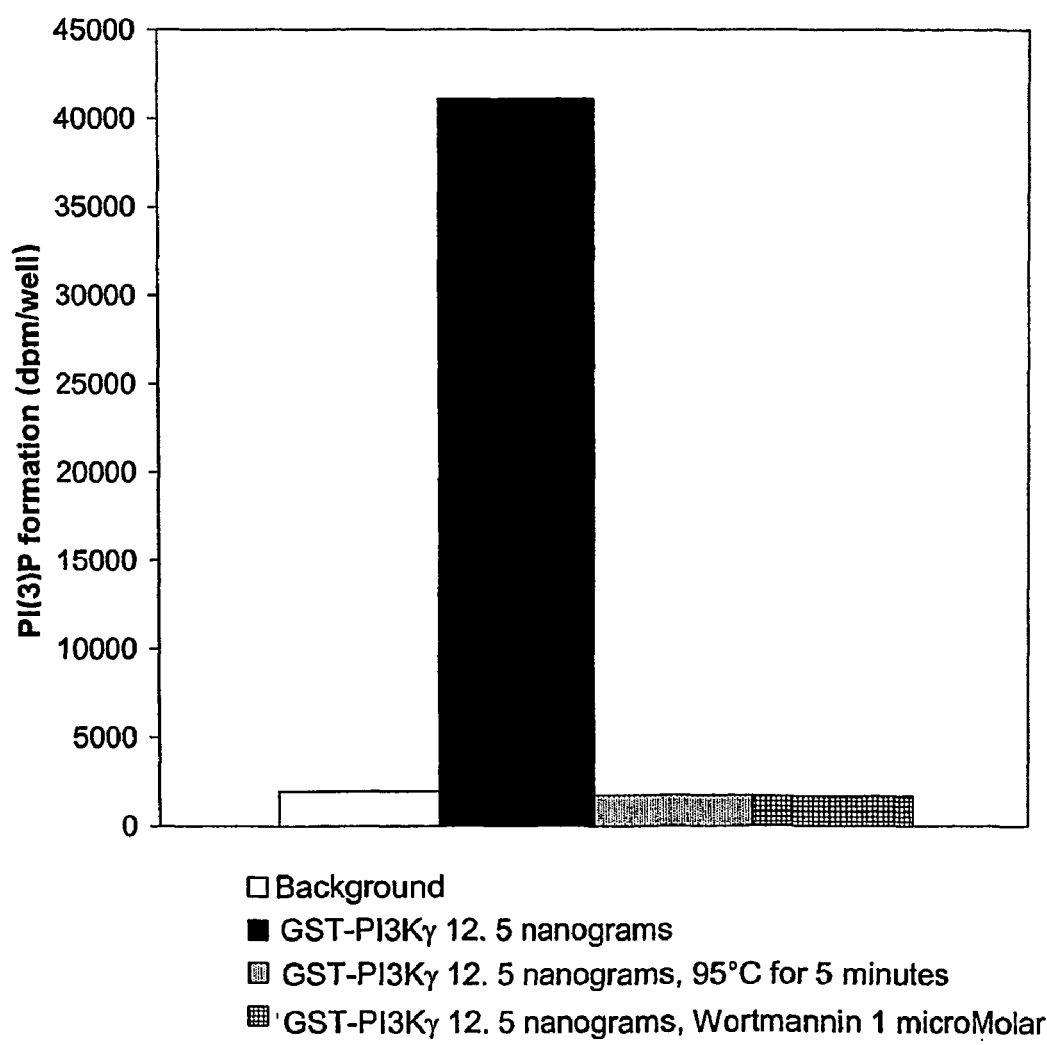
FIG. 7 shows how thermal inactivation of enzyme inhibit the formation of PI$_{(3)}$P. The 50 microliters reactions contain 12.5 nanograms of recombinant GST-PI3Kγ which was treated (or not) at 95° C. during 5 minutes, before being incubated with lipid vesicles, and in the absence or in the presence of 5 micromolar Wortmannin.

It has also been demonstrated that neomycin-coated SPA beads allow a linear increase of the recovered radiolabeled substrate up to 750 micrograms of beads per well (FIG. 6). The latter two experiments included also samples where a known PI3Kγ inhibitor called Wortmannin (Upstate Biotechnology) is added, confirming the specificity of the kinase activity detected by the means of these SPA beads. The possibility that beads itself may bind unspecifically the labeled substrate has been also excluded since a thermal treatment at 95° C., which inactivates PI3Kγ, completely brings the signal back to background levels (FIG. 7).

Figure 8:
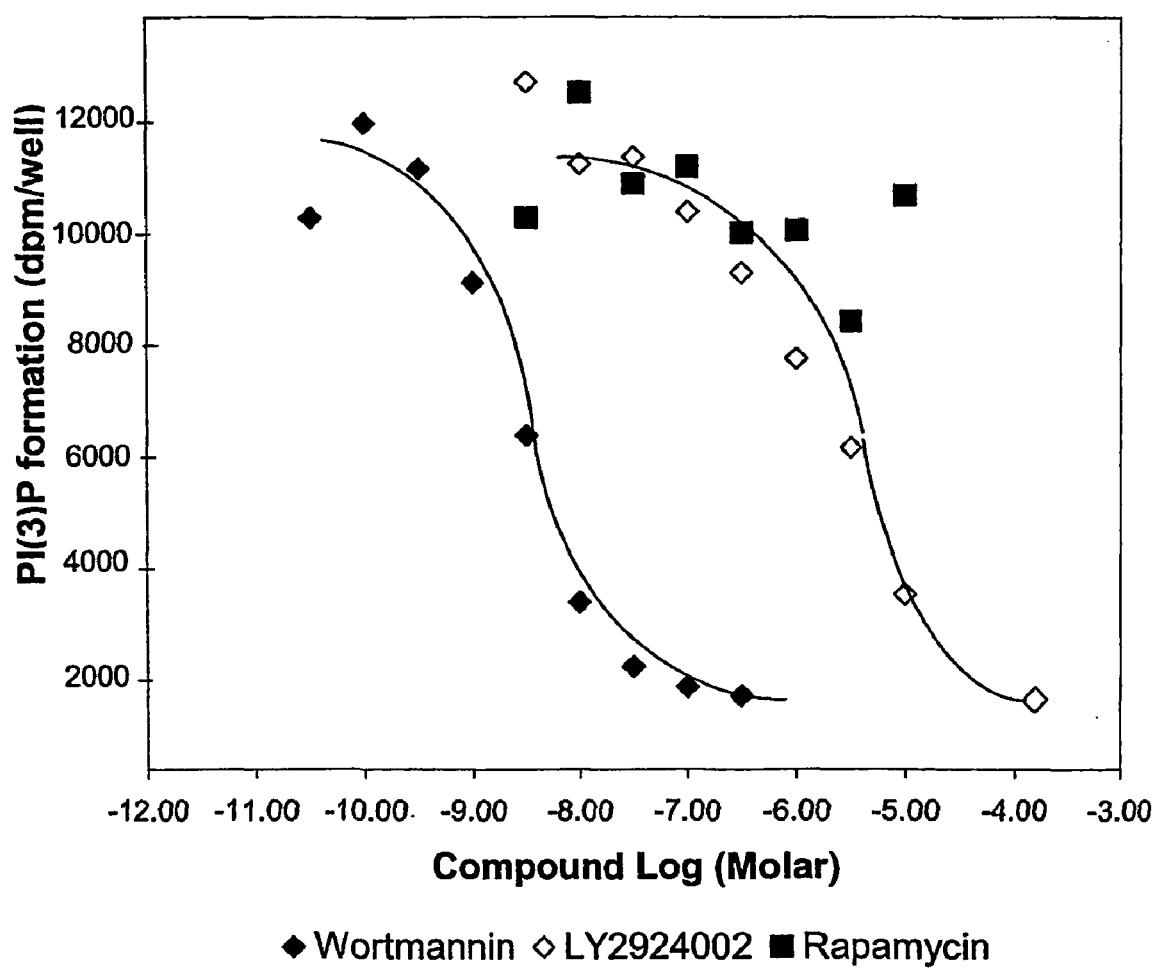
FIG. 8 shows the inhibition curves of PI3Kγ obtained using the neomycin-SPA beads and non-specific (rapamycin) or specific (Wortmannin, LY2924002) inhibitors. Increasing concentrations of Wortmannin or LY2924002 are added to 50 microliters reactions containing 12.5 nanograms of recombinant GST-PI3Kγ and lipid vesicles.

The reliability of the methods of the invention has been tested by comparing the IC$_{50}$ curves obtained using two known PI3K inhibitors (Wortmannin and LY2924002) and, as a control, rapamycin, which inhibits mTOR, a different kinase downstream in the pathway regulated by PI3Kγ. Increasing concentrations of Wortmannin or LY2924002 are added to human recombinant GST-PI3Kγ and to lipid vesicles. The IC$_{50}$ values for Wortmannin and LY2924002 (2.6 nanoMolar and 2 microMolar, respectively) which are in agreement with their published values (Stein and Waterfield, 2000), while rapamycin have no noteworthy effect (FIG. 8). These IC$_{50}$ values are not affected by the order of addition of the inhibitor and the lipid vesicles. The Km values of the enzyme for ATP and for PI have been also calculated but they are no significantly different from the values measured using the conventional methods. The signal/background ratios, Km, and IC$_{50}$ values for Wortmannin and LY2924002 calculated using either the 96-well microplate/50 microliters or the 384-well microplate/30 microliters format showed no relevant difference as well.

REFERENCES

Arbuzova A, Martushova K, Hangyas-Mihalyne G, Morris A J, Ozaki S, Prestwich G D, McLaughlin S. *Biochim Biophys Acta* (2000), 1464, 35–48.

Arcaro A, Wymann M P. *Biochem J.* (1993), 296, 297–301.

Cho J, Rando R R. *Biochemistry* (1999), 38, 8548–8554.

Comer F I and Parent C A. *Cell* (2002), 109, 541–4.

Creemer L C, Kirst H A, Vlahos C J, Schultz R M. *J Med Chem.* (1996), 39, 5021–4.

Frew T, Powis G, Berggren M., Abraham R T, Ashendel C L, Zalkow L H, Hudson C, Qazia S, Gruszecka-Kowalik E, Merriman R. *Anticancer Res* (1994), 14, 2425–2428.

Hamasaki K, Killian J, Cho J, Rando R R. *Biochemistry* (1998), 37, 656–663.

Hinchliffe K A. *Curr Biol.* (2001), 11, R371–3.

Hirsch E, Katanaev V L, Garlanda C, Azzolino O, Pirola L, Silengo L, Sozzani S, Mantovani A, Altruda F, Wymann M P. *Science* (2000), 287,1049–53.

Leevers S J, Vanhaesebroeck B, Waterfield M D. *Curr Opin Cell Biol* (1999), 11, 219–225. Llano-Sotelo B, Azucena E F, Kotra L P, Mobashery S, Chow C S. *Chem. Biol.* (2002), 9, 455–63.

Lorenzen A, Kennedy S W. *Anal Biochem.* (1993), 214, 346–8.

Meza M B. *Drug Discovery Today:HTS suppl.* (2000), 1, 38–41.

Mingeot-Leclercq M P, Tulkens P M, Brasseur R,. *Bioch. Pharmacol* (1992), 44, 1967–1975.

Powis G, Bonjouklian R, Berggren M M, Gallegos A, Abraham R, Ashendel C, Zalkow L, Matter W F, Dodge J, Grindey G, et al. *Cancer Res.* (1994), 54, 2419–23.

Riaz M, Weiner N D, Schacht, J. *J. Pharm. Sci.* (1989), 78, 172–5.

Sachetelli S, Beaulac C, Lagace J. *Bioch. Biophy. Acta* (1998), 1379, 35–41.

Schacht J., *J. Lipid Res.* (1978), 19, 1063–7.

Schacht J., *Hear. Res.* (1986), 22, 297–304.

Schroeder R, Waldsich C, Wank H. *EMBO J* (2000),19, 1–9.

Simonsen A, Wurmser A E, Emr S D, Stenmark H. *Curr Opin Cell Biol* (2001), 13, 485–92.

Stein R C and Waterfield M D. *Mol Med Today* (2000), 6, 347–357.
Sundberg S A. *Curr Opin Biotechnol* (2000), 11, 47–53.
Van Bambeke F, Tulkens P M, Brasseur R, Mingeot-Leclercq M P. *Eur J Pharnacol*. (1995), 289, 321–33.
Xu Y, Seet L F, Hanson B, Hong W. *Biochem J*. (2001), 360, 513–530.
Walter F, Vicens Q, Westhof E. *Curr Opin Chem Biol*. (1999), 3, 694–704.
Wang Y, Killian J, Hamasaki K, Rando R R. *Biochemistry* (1996), 35, 12338–12346
Ward S G. *Methods Mol. Biol*. (2000), 138,163–172.
Zembower T R, Noskin G A, Postelnick M J, Nguyen C, Peterson L R. *Int J. Antimicr. Agents* (1998), 10, 95–105.

The invention claimed is:

1. A method for identifying and/or quantifying radiolabeled Aminoglycoside Binding Molecules (ABMs) in a sample, said method comprising the following steps:
    a) preparing a sample comprising at least an ABM and an enzyme;
    b) allowing said enzyme either to add a radiolabeled group present in the sample to the ABM, or to cleave a radiolabeled group present in the ABM;
    c) incubating the sample with one or more solid supports impregnated with a scintillant compound and covered with an aminoglycoside; and
    d) measuring the level of emission generated by the one or more scintillating supports; and
    e) correlating said level of emission to the presence or amount of said radiolabeled Aminoglycoside Binding Molecules to identify and/or quantify radiolabeled ABM's.

2. The method of claim 1 wherein the sample and the one or more support (s) are separated between steps (c) and (d).

3. The method of claim 1 wherein different samples prepared according to step (a) comprise equal amount of the ABM, equal amount of the enzyme that either adds a radiolabeled group present in the sample to the ABM or cleaves a radiolabeled group present in the ABM, and wherein said different samples are prepared with or without one or more candidate inhibitors of the enzyme or of the interaction between the ABM and the aminoglycoside which are added before or during step (c).

4. An assay for identifying and/or quantifying compounds which modulate an interaction between an ABM and an enzyme that adds a radiolabeled group present in the sample to the ABM or cleaves a radiolabeled group present in the ABM, wherein the radiolabeled ABM is identified and/or quantified according to the method of claim 3.

5. The assay of claim 4 wherein the compounds are potential inhibitors of the enzyme.

6. The assay of claim 4, wherein the compounds are aminoglycoside-modifying bacterial enzymes.

7. The assay of claim 4 wherein the one or more supports are beads.

8. The assay of claim 4 wherein the aminoglycoside is neomycin.

9. The assay of claim 4 wherein the ABM is a mono- or polyphosphatated phosphoinositide.

10. The assay of claim 9 wherein the enzyme is a phosphoinositide kinase.

11. The assay of claim 4 wherein the ABM is an RNA molecule.

12. An assay for identifying and/or quantifying compounds which modulate an interaction between an ABM and an aminoglycoside, said assay comprising quantifying radiolabeled ABM according to the method of claim 3.

13. The method of claim 1 wherein different samples prepared according to step (a) comprise equal amount of the ABM, equal amount of the enzyme that either adds a radiolabeled group present in the sample to the ABM or cleaves a radiolabeled group present in the ABM, with or without one or more candidate inhibitors of the enzyme or of the interaction between the ABM and the aminoglycoside added before or during step (c).

14. The method of claim 1 wherein different samples prepared according to step (a) comprise equal amount of the ABM, and different mixtures of molecules potentially containing an enzyme that either adds a radiolabeled group present in the sample to the ABM or cleaves a radiolabeled group present in the ABM.

15. The method of claim 1 wherein different samples prepared according to step (a) comprise equal amount of an enzyme that either adds a radiolabeled group present in the sample to the ABM or cleaves a radiolabeled group present in the ABM, and different mixtures of molecules potentially containing an ABM.

16. An assay for identifying and/or quantifying an enzyme that either adds a radiolabeled group present in the sample to the ABM or cleaves a radiolabeled group present in the ABM, wherein the radiolabeled ABM is identified and/or quantified according to the method of claim 1.

17. An assay for identifying and/or quantifying an ABM, said assay comprising quantifying radiolabeled ABM according to the method of claim 1.

18. A kit for identifying and/or quantifying aminoglycoside binding molecules, enzymes modifying said molecules, or compounds modulating the interaction between ABMs and either enzymes or aminoglycosides, comprising a scintillating solid support covered with an aminoglycoside.

* * * * *